(12) United States Patent
Landis (10) Patent No.: US 10,211,667 B2
(45) Date of Patent: Feb. 19, 2019

(54) UNINTERRUPTED POWER SUPPLY SYSTEMS AND METHODS

(71) Applicant: PILLER USA, INC., Middletown, NY (US)

(72) Inventor: Ronald Landis, Austin, TX (US)

(73) Assignee: Piller USA, Inc., Austin, TX (US)

(*) Notice: Subject to any disclaimer, the term of this patent is extended or adjusted under 35 U.S.C. 154(b) by 336 days.

(21) Appl. No.: 14/875,081

(22) Filed: Oct. 5, 2015

(65) Prior Publication Data
US 2016/0099607 A1 Apr. 7, 2016

Related U.S. Application Data

(60) Provisional application No. 62/059,467, filed on Oct. 3, 2014.

(51) Int. Cl.
*H02J 1/12* (2006.01)
*H02J 3/32* (2006.01)
(Continued)

(52) U.S. Cl.
CPC ............. *H02J 7/34* (2013.01); *A61K 9/0019* (2013.01); *A61K 31/568* (2013.01); *G06F 1/26* (2013.01);
(Continued)

(58) Field of Classification Search
CPC ...... G06F 1/26; G06F 1/28; G06F 1/24; H02J 7/00; H02J 7/34; H02J 7/35; H02J 7/345;
(Continued)

(56) References Cited

U.S. PATENT DOCUMENTS 5,932,935 A 8/1999 Clifton et al.
9,276,410 B2 * 3/2016 Binder ............... H02J 3/383
(Continued)

FOREIGN PATENT DOCUMENTS

EP 2565296 A1 3/2013

OTHER PUBLICATIONS

Active Power Investor Relations Press Release, http://ir.activepower.com/phoenix_zhtml?c = 122065&p = irolnewsArticle_print&ID= 1975891, Oct. 9, 2014, pp. 1 to 2.
(Continued)

*Primary Examiner* — Fritz M Fleming
*Assistant Examiner* — Jagdeep Dhillon
(74) *Attorney, Agent, or Firm* — Pillsbury Winthrop Shaw Pittman LLP (57) ABSTRACT

Provided in some embodiments is an uninterruptable electrical power supply system. The system includes an electrical power distribution network (having a consumer side network coupled to one or more electrical loads that consume electrical power and a utility side network that supplies electrical power to the consumer side network), a primary power source (coupled to the utility side network, and that supplies electrical power to the utility side network for supply to the consumer side network), a secondary power source coupled to the utility side network, and a terminal between the consumer side network and the utility side network. The secondary power source supplies backup power to the utility side network (in response to a power shortage on the utility side network) and sinks surplus power from the utility side network (in response to a power surplus on the utility side network).

28 Claims, 5 Drawing Sheets

(51) Int. Cl.

| | | |
|---|---|---|
| *H02J 3/34* | (2006.01) | |
| *H02J 7/34* | (2006.01) | |
| *G06F 1/26* | (2006.01) | |
| *H02J 3/30* | (2006.01) | |
| *A61K 9/00* | (2006.01) | |
| *A61K 31/568* | (2006.01) | |
| *H02J 15/00* | (2006.01) | |
| *H02J 7/00* | (2006.01) | |

(52) U.S. Cl.
CPC ............... *H02J 3/30* (2013.01); *H02J 7/345* (2013.01); *H02J 15/00* (2013.01); *H02J 7/00* (2013.01)

(58) Field of Classification Search
CPC .......... H02J 7/0065; H02J 7/0052; H02J 9/00; H02J 9/06; H02J 3/00; H02J 3/383; H02J 3/30; H02J 2003/007
USPC ..... 307/46, 82, 80, 86, 66, 38, 43; 700/286; 705/400; 702/63
See application file for complete search history.

(56) References Cited

U.S. PATENT DOCUMENTS

| | | | |
|---|---|---|---|
| 9,705,333 B2* | 7/2017 | Clifton | G05F 1/66 |
| 9,735,613 B2* | 8/2017 | Orthlieb | H02J 3/00 |
| 2002/0103655 A1* | 8/2002 | Boies | G06Q 10/06375 700/291 |
| 2005/0122084 A1 | 6/2005 | Pinkerton, III et al. | |
| 2007/0005192 A1* | 1/2007 | Schoettle | H02J 3/32 700/286 |
| 2007/0022755 A1 | 2/2007 | Pinkerton et al. | |
| 2009/0043520 A1* | 2/2009 | Pollack | B60L 3/12 702/62 |
| 2010/0171366 A1 | 7/2010 | Perkins | |
| 2011/0010043 A1* | 1/2011 | Lafky | B60L 11/1842 701/31.4 |
| 2011/0215645 A1 | 9/2011 | Schomburg et al. | |
| 2011/0285546 A1* | 11/2011 | Vadali | G01D 4/002 340/870.16 |
| 2013/0024034 A1* | 1/2013 | Iino | H02J 3/383 700/291 |
| 2013/0054036 A1* | 2/2013 | Cherian | G06Q 10/06 700/286 |
| 2013/0110300 A1 | 5/2013 | Sinsabaugh | |
| 2013/0113287 A1 | 5/2013 | Singh et al. | |
| 2013/0193928 A1 | 8/2013 | Prosser | |
| 2014/0012429 A1* | 1/2014 | Dempster | G05F 5/00 700/295 |
| 2014/0265606 A1* | 9/2014 | Gazit | H02J 7/0018 307/82 |
| 2014/0366684 A1 | 12/2014 | Schuetze | |

OTHER PUBLICATIONS

Large Hybrid Rotary Uninterruptible Power Supply, https://web.archive.org/web/20140612032302/http://www.pscpower.com/whatwedo/products/uninterruptiblepowersupply/seriesxclargehybridrotaryups/, Jun. 12, 2014, pp. 1 to 2.

Ultracapacitor-Based Uninterrupted Power Supply System, http://www.techbriefs.com/component/content/article/10133, Jun. 1, 2011, pp. 1 to 2.

International Search Report and Written Opinion for Related PCT Application PCT/US2015/054004, dated Jan. 5, 2016, pp. 1-13.

International Preliminary Report on Patentability for Related PCT Application PCT/US2015/054004, dated Apr. 4, 2017, pp. 1 to 8.

* cited by examiner

UNINTERRUPTED POWER SUPPLY SYSTEMS AND METHODS

CROSS-REFERENCE TO RELATED APPLICATIONS

The present application is a non-provisional of, and thus claims the benefit of, U.S. Provisional Patent Application 62/059,467, titled Uninterrupted Power Supply Systems and Methods, filed 3 Oct. 2014, the contents of which are hereby incorporated by reference in their entirety.

BACKGROUND OF THE INVENTION

1. Field of the Invention

This invention relates generally to power systems and more particularly to uninterruptible power systems.

2. Description of the Related Art

A basic function of an uninterruptible power system ("UPS") is to ensure continued delivery of power to loads (e.g., appliances, electronics, industrial equipment, etc.), even under a variety of primary power fault conditions and disturbances. A UPS may include, for example, a primary power source (e.g., an alternating current (AC) utility source delivered from a power grid) that provides power to loads, and a secondary power source (e.g., a battery or an AC generator) that can provide additional power to supplement the primary power source. Under "normal" operating conditions (e.g., when the primary power source is operating within defined, acceptable, operating limits of voltage and frequency), power for loads can be provided by the primary power source. Under "abnormal" operating conditions (e.g., when the primary power source is not operating within defined, acceptable, operating limits of voltage and frequency), the power for loads can be provided (at least partially) by the secondary power source. For example, in the event the primary power source fails, the secondary power source can be used to power to the loads.

Although alternative energy sources (e.g., solar power, wind power, hydro power, geothermal power, and the like) are increasing in use and popularity, they often contribute to degradation in the quality of the AC power provided by a power grid. Compared to conventional large-scale AC power generation facilities, alternative power sources are more likely to exhibit power interruptions and power quality issues, thereby contributing to a variety of power line disturbances (e.g., power sags, power surges, undervoltage or overvoltage conditions, transients associated with source switching on the utility line, utility line noise, frequency variations, harmonic distortion, line brownouts, line dropouts and the like). Unfortunately, contemporary loads (e.g., electronic loads) often require an uninterrupted flow of high quality AC power. For example, electronic components may require a supply of AC power that is within a given voltage and frequency ranges. Thus, it is desirable to provide a UPS that can reduce or eliminate the effects of line disturbances on the quality of the AC power it delivers.

SUMMARY OF THE INVENTION

This summary is provided to introduce a selection of concepts in a simplified form that are further described below in the Detailed Description. This Summary is not intended to identify key features or essential features of the claimed subject matter, nor is it intended to be used to limit the scope of the claimed subject matter.

Various embodiments of methods and apparatus for supplying power are provided herein. In some embodiments, provided is an uninterruptable electrical power supply system. The UPS includes an electrical power distribution network including: a consumer side network configured to couple to one or more electrical loads configured to consume electrical power; a utility side network configured to supply electrical power to the consumer side network; and a terminal coupled between the consumer side network and the utility side network; a primary power source coupled to the utility side network, wherein the primary power source is configured to supply electrical power to the utility side network for supply to the consumer side network; and a secondary power source coupled to the utility side network, wherein the secondary power source is configured to: supply, in response to a power shortage on the utility side network, backup power to the utility side network; and sink, in response to a power excess on the utility side network, power from the utility side network.

In some embodiments, provided is uninterruptable electrical power supply system including: a secondary power source configured to be coupled to a power distribution network including a primary power source configured to supply electrical power to the power distribution network, wherein the secondary power source is configured to: supply, in response to a power shortage on the utility side network, backup power to the utility side network; and sink, in response to a power excess on the utility side network, power from the utility side network.

In some embodiments, provided is a method for providing uninterrupted power via a power distribution network including a secondary power source configured to supply backup power to the power distribution network, the method including operating the secondary power source to: supply, in response to a power shortage on the utility side network, backup power to the utility side network; and sink, in response to a power excess on the utility side network, power from the utility side network.

While the invention is susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

As discussed in more detail below, provided in some embodiments are uninterruptable power systems and associated methods. In some embodiments, an uninterrupted power system includes a power distribution network, a primary power source, and a secondary power source. The power distribution network can be used to provide power to loads. The power distribution network may include two parts—a "utility side" that is includes devices for supplying power, and a "consumer side" that includes loads (e.g., electrical devices) that consume the supplied power. In some embodiments, the primary power source is operated to provide power to the power distribution network under normal conditions, and the secondary power source is operated to provide backup power (e.g., supplemental power) in the event a power deficiency/shortage exists on the network (e.g., during a voltage drop on the network) or to sink power (e.g., absorb or dissipate power) in the event a power excess/surplus exists on the network (e.g., during a voltage spike on the network). In some embodiments, the primary and secondary sources are both provided on the "utility side" of the network.

In some embodiments, the secondary power source includes one or more power driver circuits that are capable of supplying power to the power distribution network and/or sinking power from the power distribution network. In certain embodiments, a power driver circuit includes a power conditioner circuit (e.g., a storage capacitor configured to store energy in an electrical form), a mechanical energy circuit (e.g., a mechanical energy storage device configured to store energy in a mechanical form), a chemical energy circuit (e.g., a chemical energy storage device configured to store energy in a chemical form), and/or a power dissipation circuit (e.g., a device used to dissipate energy). In some embodiments, the secondary power source includes a plurality of power driver circuits coupled in parallel to the power distribution network. Such an embodiment may be advantageous as it can enable a larger quantity of power to be supplied to the power distribution network. For example, four 750 Watt (W) power driver circuits can be coupled to a power distribution network to provide approximately four times the power that can be supplied by a single power driver circuit (e.g., supply approximately 750 W approximately four times the duration, or approximately 3000 W for approximately the same duration).

In some embodiments, the mechanical energy circuit includes a flywheel system including flywheel that is rotated to store mechanical energy, a motor that drives rotation of the flywheel (e.g., using power supplied by the network, such as the power supplied to the network by primary power source), and a generator that converts mechanical energy of the flywheel into electrical energy (e.g., electrical energy to be supplied to the utility side network as supplemental/backup power). In some embodiments, the chemical energy circuit includes one or more batteries, a bank of batteries, an ultracapacitor, and/or the like. In some embodiments, the power dissipation circuit includes a resistance device (e.g., a resistor) configured to dissipate energy, e.g., in the form of heat.

In some embodiments, the secondary power source is operated to supply backup power in a prioritized/hierarchical manner. For example, the secondary power source may (1) in response to a first level power shortage (e.g., a minor voltage/frequency drop) supply backup power derived from the electrical energy stored by the storage capacitor, (2) in response to a second level power shortage (e.g., a moderate voltage/frequency drop), supply backup power derived from the energy stored by the mechanical energy storage device, and (3) in response to a third level power shortage (e.g., a major voltage/frequency drop), supply backup power derived from the energy stored by the chemical energy storage device. Such a system may be advantageous as it can help to extend the life of components that are susceptible to degradation. For example, a capacitor may be suited for frequent uses as a power source ("hits"), a flywheel system may be less suited for frequent hits than a capacitor, and batteries may be less suited for frequent hits than both a capacitor and a flywheel system. As a result, a battery's performance may degrade at a relatively high rate when compared to the other power storage devices and may need to be replaced more frequently if they are frequently used to service hits. Having to replace batteries can add a significant amount of cost to a system. By prioritizing the hits to the various components in a hierarchical manner, components that are susceptible to degradation (e.g., batteries) can be used less often to service hits, whereas components that are less susceptible to degradation (e.g., a capacitor) can be used more often to service hits.

Figure 1:
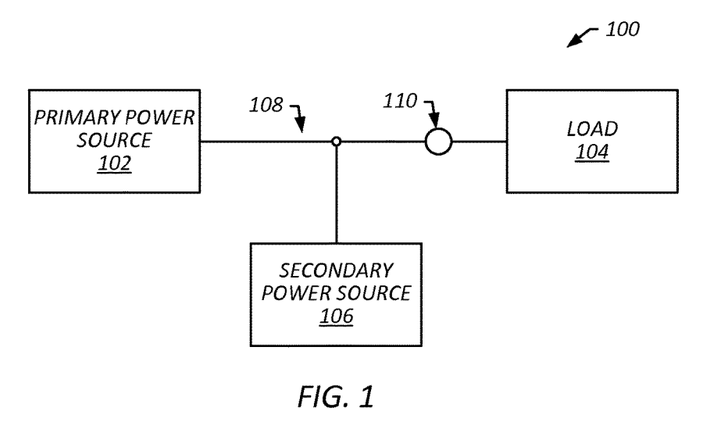
FIG. 1 is a diagram that illustrates an uninterruptable power system ("UPS") in accordance with one or more embodiments of the present technique.

FIG. 1 is a diagram that illustrates an uninterruptable power system ("UPS") 100 in accordance with one or more embodiments of the present technique. In some embodiments, UPS 100 includes a primary power source ("primary source") 102, a load 104, and a secondary power source ("secondary source") 106 electrically coupled via an electrical power distribution network ("distribution network") 108 including a terminal 110. Primary source 102, secondary source 104 and distribution network 108 may be referred to as an "electrical grid."

Primary source 102 may include one or more AC utility sources for providing power to load 104. In some embodiments, primary source 102 is intended to provide power under most if not all circumstances. In some embodiments, primary source 102 includes one or more AC utility sources that generate AC power for distribution via the electrical power grid 108. Traditional AC utility power sources may include electrical power stations, such as a coal fired power plant, natural gas fired power plant, a nuclear power plant, hydro-electric power plant, and/or the like. Alternative AC power sources may include a solar power (PV) system (e.g., a solar farm), a wind power system (e.g., a wind farm), a geothermal power system, a bio-fuel power system, a diesel power system (e.g., a diesel generator), and/or the like. Primary source 102 may include any combination of traditional and/or alternative AC utility sources.

Secondary source 104 may include one or more AC utility sources that can provide power to distribution network 108 to supplement or in place of power provided by primary source 102 to distribution network 108 for powering load 104. In some embodiments, under "normal" operating conditions (e.g., when primary source 102 is supplying power within defined, acceptable, operating limits of voltage and frequency), load 104 is powered using electrical power supplied by primary source 102. For example, if primary source 102 is supplying sufficient power (e.g., primary source 102 is supplying power within defined, acceptable, operating limits of voltage and frequency), load 104 may be powered entirely using the power supplied by primary source 102 ("primary power"). That is, if UPS 100 is operating under "normal" conditions load 104 may not receive power from secondary source 106. In some embodiments, under "abnormal" operating conditions (e.g., when primary source 102 is not supplying power within defined, acceptable, operating limits of voltage and frequency), load 104 is powered (at least partially) using electrical power supplied by secondary source 106 ("secondary power"). For example, if primary source 102 is not supplying sufficient power (e.g., primary source 102 is not supplying power within defined, acceptable, operating limits of voltage and frequency), load 104 may be powered entirely using the power supplied by secondary source 106, or a combination of primary power supplied by secondary source 106 and secondary power supplied by secondary source 106. That is, if UPS 100 is not operating under "normal" conditions load 104 may receive some or all of its operating power from secondary source 106.

In some embodiments, secondary source is housed in a container unit. For example, secondary source may be housed in a portable/modular enclosure such as those manufactured by Active Power, Inc., having headquarters in Austin, Tex. Such a portable/modular enclosure may enable secondary source to be moved into location and coupled to the distribution network (or removed) with little to no modification to the distribution network infrastructure. For example, an I/O line and control bus of the secondary source extending from the enclosure may be simply tied to an existing power line of the distribution network. In some embodiments, the housing does not include any components of a primary power source. Thus, the secondary source may be brought on-line and/or removed with minimal to no disturbances to the primary power source.

Load 104 may include one or more loads that consume AC electrical power. For example, load 104 may include electrical devices/systems, such as appliances, lights, electronics, industrial equipment, and/or the like. Load 104 may operate using electrical power provided on distribution network 108, including the power supplied to distribution network 108 by primary source 102 and/or secondary source 106.

Distribution network 108 may include an interconnected electrical network for delivering electricity from suppliers (e.g., primary source 102 and secondary source 106) to consumers (e.g., load 104). For example, distribution network 108 may include electrical transmission/distribution lines that carry power from sources to loads. In some embodiments, the distribution network may include a "utility side" and a "consumer side." The utility side may include a portion of the network that extends from power sources to an electrical terminal (e.g., terminal 110) that couples loads to the grid. The consumer side may include a portion of the network that extends from the terminal to the loads. Terminal 110 may include, for example, a power meter. During operation, a utility side may carry power from the source(s) to the terminal, and the consumer side may carry/distribute power from the terminal to the loads. For example, in the context of a home or business, the utility side may include a power line that terminates into a meter (terminal), and the consumer side may include electrical lines (e.g., wiring, breaker boxes, electrical outlets and the like) that extend from the meter (terminal) to loads at the residence or business (e.g., appliances, lights, electronics, industrial equipment, and/or the like). The utility side may be operated by a utility (e.g., a power company). The consumer side may be operated by the consumer (e.g., the home or business owner may be responsible for maintaining the consumer side). Although the illustrated embodiment depicts the secondary power source coupled to the utility side, embodiments may include one or more secondary power sources coupled to the consumer side of the network, in place or in addition to secondary sources coupled to the utility side of the network.

In some embodiments, UPS 100 may include a microgrid. A microgrid, in some embodiments, is a power system (e.g., sources, loads and/or a distribution network) that is operated independent of traditional utility grids. For example, in a microgrid configuration, UPS 100 may be isolated from traditional AC utility sources, and rely on power provided alternative AC power sources. In some embodiments, for example, primary power source 102 may include alternative AC power sources, but may not include traditional AC utility sources. Thus, a residential microgrid may include, for example, a privately owned and operated solar power farm primary source (e.g., including multiple solar panels) and diesel generator primary source, a secondary power source (e.g., an energy storage device such as a flywheel system and/or batteries), and a distribution network that distributes power to loads throughout the residence (e.g., power lines/wire that route power to appliances, lights, electronics, and so forth). In some instances, a microgrid may be supplemented by traditional AC power sources. For example, the distribution network of a microgrid may be coupled to an AC utility power grid such that it can draw supplemental power from the grid if needed. In some instances, a microgrid may be capable of supplementing traditional AC power sources. For example, the distribution network of a microgrid may be coupled to an AC utility power grid such that it can supply excess power to the grid.

In some embodiments, secondary power source 106 includes a power driver circuit that is capable of receiving energy, storing energy, supplying energy, and/or dissipating energy. For example, secondary power source 106 may include a power driver circuit that is capable of receiving energy from distribution network 108, storing at least some of the received energy, supplying energy to distribution network 108, and/or dissipating energy received from distribution network 108. In some embodiments, the power driver circuit may include an energy storage device that is capable of storing energy, supplying energy, and/or absorbing energy. For example, in some embodiments, the energy storage device may include a battery and/or a flywheel system (e.g., a flywheel motor/generator), such as that described in U.S. Pat. No. 5,932,935 by Clifton et al., and titled Energy Storage Flywheel Emergency Power Source and Methods (the '935 Patent), which is hereby incorporated by reference. During operation of a flywheel motor/generator, a flywheel (e.g., a disc) may rotate to store mechanical energy. In some embodiments, the rotation is imparted and maintained by a motor driven using power supplied by another energy source, such electrical energy provided by the primary energy source of the UPS. In some embodiments, in the event electrical energy is needed (e.g., the primary power source is operating abnormally causing a power shortage—such as during voltage drop), the mechanical energy stored by the rotation of the flywheel can be converted to electrical energy that is supplied to the distribution network. Conversely, in some embodiments, in the event excess electrical energy needs to be absorbed/dissipated (e.g., the primary power source is operating abnormally causing a power surplus—such as a voltage spike), the excess electrical energy supplied to the distribution network by the primary source can be used to drive the motor, thereby enabling the power driver circuit to absorb/dissipate the excess energy via conversion of the electrical energy to mechanical energy via rotation of the flywheel. In some embodiments, the power driver circuit includes an energy dissipation circuit that is devoted to dissipating excess energy.

Figure 2:
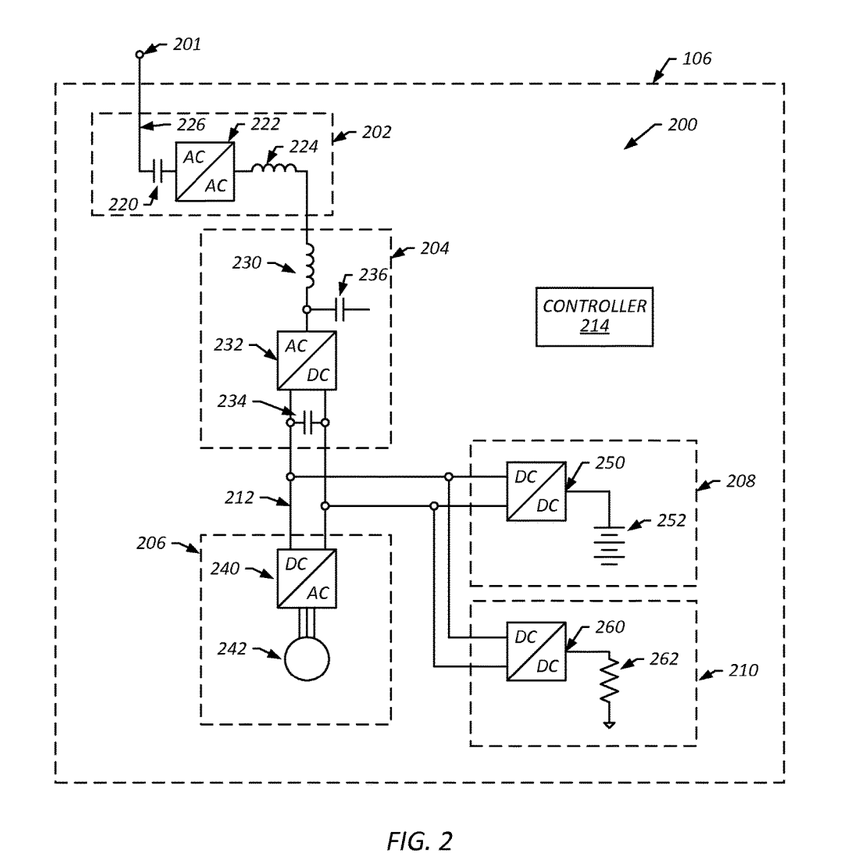
FIG. 2 is a diagram that illustrates secondary power source in accordance with one or more embodiments of the present technique.

FIG. 2 is diagram that illustrates secondary power source 106 in accordance with one or more embodiments of the present technique. In the illustrated embodiment, secondary power source 106 includes a power driver circuit 200 including an input/output terminal 201, an input/output circuit 202, a power conditioner circuit 204, a mechanical energy circuit 206, a chemical energy circuit 208, a power dissipation circuit 210, a direct current (DC) bus 212, and a power driver controller ("controller") 214. Input/output terminal 201 may be electrically coupled to distribution network 108.

In some embodiments, input/output (I/O) circuit 202 is employed to control and/or condition power that is received from and/or supplied to distribution network 108. In the illustrated embodiment, input/output circuit 202 includes a line capacitor 220, an I/O converter 222, and a block choke 224 coupled to an AC I/O line 226. In some embodiments, line capacitor 220 includes a capacitor that is employed to smooth/stabilize the power flow between distribution network 108 and power driver circuit 200. In some embodiments, I/O converter 222 includes an AC-AC converter circuit that can adjust the voltage and frequency of the AC power passing there through. In some embodiments, block choke 224 includes an inductor that is employed to buffer/dampen energy carried on AC I/O line.

In some embodiments, power conditioner circuit 204 is employed to condition power as it travels between I/O circuit 202 and respective ones of mechanical energy circuit 206, chemical energy circuit 208 and power dissipation circuit 210 and/or store energy that can be supplied to distribution network 108. In the illustrated embodiment, power conditioner circuit 204 includes a filter choke 230, a utility converter 232, a DC storage capacitor 234 and an AC line capacitor 236.

In some embodiments, filter choke 230 includes an inductor employed to remove AC ripple.

In some embodiments, utility converter 230 includes a rectifier circuit employed to convert three-phase AC power input (e.g., AC power received from distribution network 108) into DC power output to DC bus 212, and/or an inverter circuit employed to convert DC power received from DC bus 212 to three-phase AC power output to I/O line 201 (e.g., AC power for output to distribution network 108).

In some embodiments, DC storage capacitor 234 includes a capacitor connected across DC bus 212 and employed to store DC power. During operation, DC storage capacitor 234 may be charged to a pre-determined nominal DC voltage. During operation, DC storage capacitor 234 may supply substantially all of the reactive load current as well as transient currents that do not cause the DC bus voltage to decline below a pre-determined level.

In some embodiments, AC storage capacitor 236 includes a capacitor coupled to the AC line 226.

In some embodiments, mechanical energy circuit 206 is employed to store energy, generate power that can be supplied to distribution network 108, and/or to absorb/dissipate excess energy present on distribution network 108. In the illustrated embodiment, mechanical energy circuit 206 includes a mechanical converter 240 and a mechanical energy device 242.

In some embodiments, mechanical converter 240 includes a rectifier circuit employed to convert three-phase AC power input (e.g., AC power received from mechanical energy device 242) into DC power supplied to DC bus 212, and/or an inverter circuit employed to convert DC power received from DC bus 212 to three-phase AC power output (e.g., AC power for output for consumption by mechanical energy device 202).

In some embodiments, mechanical energy device 242 includes a backup AC a flywheel system, such as that described in the '935 Patent. Mechanical energy device 242 may be configured to receive energy, store energy, and/or supply energy. For example, in an embodiment in which mechanical energy device 242 includes a flywheel system, during operation, a flywheel (e.g., a disc) of the flywheel system may be rotated at an operational speed (e.g., 6000 revolutions per minute (rpm)) such that mechanical energy is stored via rotation of the flywheel. In some embodiments, rotation of the flywheel is imparted and maintained by a motor of the flywheel system that is driven using power supplied by another energy source, such electrical power received from the distribution network (e.g. supplied by primary source 102 via I/O circuit 202, power conditioner circuit 204 and DC bus 212). In some embodiments, in the event supplemental electrical energy is needed (e.g., a voltage drop occurs on distribution network 108), mechanical energy stored via rotation of the flywheel can be converted (e.g., by a generator of the flywheel motor/generator) to electrical energy that is supplied to distribution network 108 (e.g., via DC bus 212, power conditioner circuit 204, and I/O circuit 202). Conversely, in some embodiments, in the event excess electrical energy needs to be absorbed/dissipated (e.g., a voltage spike occurs on distribution network 108), the excess electrical energy can be used to drive the motor, thereby enabling the power driver circuit to absorb/dissipate the excess energy via conversion of the electrical energy to mechanical energy (e.g., in the form of rotation of the flywheel).

In some embodiments, the mechanical energy device 242 is operated at a reduced capacity such that the additional capacity can be used to absorb/dissipate the excess energy. For example, the flywheel of the flywheel system may be operated at a reduced operational speed (e.g., below maximum rated operational limits) such that the rotational speed of the flywheel can be increased to absorb/dissipate the excess energy. In some embodiments, for example, despite the flywheel having a rated operational speed of 7700 rpm ("rotations per minute"), the flywheel is maintained at a reduced operational speed of 6000 rpm during normal operating conditions. In the event, power driver circuit 200 needs to absorb/dissipate excess energy (e.g., from distribution network 108), the excess energy can be used to power the motor, thereby causing an increase in the speed of the flywheel that absorb the energy. In some embodiments, the speed of the flywheel can be subsequently reduced (e.g., reduced to 6000 rpm), thereby allowing the flywheel to continue to absorb/dissipate excess energy. In some embodiments, mechanical energy circuit 206 is employed to supply power that cannot be supplied by other energy sources of driver circuit 200 (e.g., capacitor 234, capacitor 236 and/or chemical energy circuit 208), up to the total real and reactive power required by load 104.

In some embodiments, chemical energy circuit 208 is employed to store energy and/or generate power that can be supplied to distribution network 108. In the illustrated embodiment, chemical energy circuit 208 includes a chemical converter 250 and a chemical energy device 252.

In some embodiments, chemical converter 250 is employed to control the flow of energy between DC bus 212 and chemical energy device 252. Chemical converter 250 may include a DC-DC converter (e.g., a boost converter).

In some embodiments, chemical energy device 252 includes a battery (e.g., a single battery, a battery bank), an ultracapacitor and/or the like. In some embodiments, chemical converter 250 includes a DC-DC converter (e.g., a DC boost converter) employed to convert voltage levels between DC bus 212 and chemical energy device 252. In some embodiments, chemical converter 250 includes charging circuitry that provides for charging chemical energy device 252 using power present on DC bus 212 and/or a discharge circuitry that provides for supplying power to the DC bus 212 using energy stored in chemical energy device 252. For example, in an embodiment in which chemical energy device 252 includes a battery, chemical converter 250 may be operated to charge and/or maintain a charge of the battery. In some embodiments, charging of the battery is accomplished using power supplied by another energy source, such electrical power received from the distribution network (e.g. supplied by primary source 102). In some embodiments, in the event supplemental electrical energy is needed (e.g., a voltage drop occurs on distribution network 108), chemical converter 250 may be operated to convert the chemical energy stored in the battery to electrical energy (power) that is supplied to distribution network 108 (e.g., via DC bus 212, power conditioner circuit 204, and I/O circuit 202). In some embodiments, chemical energy circuit 208 is employed to supply power that cannot be supplied by other energy sources of driver circuit 200 (e.g., capacitor 234, capacitor 236 and/or mechanical energy circuit 206), up to the total real and reactive power required by load 104.

In some embodiments, power dissipation circuit 210 is employed to dissipate excess energy. In the illustrated embodiment, power dissipation circuit 210 includes a dissipation converter 260 and a dissipation device 262. In some embodiments, dissipation converter 260 is employed to control the flow of energy from DC bus 212 to dissipation device 262. In some embodiments, dissipation converter 260 includes a DC-DC converter (e.g., a DC boost converter) employed to convert voltage levels between DC bus 212 and dissipation device 262.

In some embodiments, dissipation device 262 includes a resistor or similar device. During operation, in the event excess electrical energy needs to be dissipated (e.g., a voltage spike occurs on distribution network 108), the excess electrical energy may be directed to power dissipation circuit 210 and through dissipation device 262, thereby enabling the power driver circuit to absorbed/dissipate the excess energy.

Dissipation via power dissipation circuit 210 can be accomplished separate from or in parallel with absorption/dissipation of energy via other elements power driver 200, such as mechanical energy circuit 206. For example, in the event a relatively small voltage spike occurs that either of power dissipation circuit 210 or mechanical energy circuit 206 has the capacity to absorb/dissipate, the excess energy associated with the spike may be absorbed/dissipated entirely by either one of power dissipation circuit 210 or mechanical energy circuit 206. In the event a relatively large voltage spike occurs, the excess energy associated with the spike may be absorbed in part by power dissipation circuit 210 and in part by mechanical energy circuit 206. This may be particularly advantageous if the excess energy created by the spike exceeds the respective absorption/dissipation capacities of power dissipation circuit 210 and mechanical energy circuit 206.

In some embodiments, controller 214 monitors the various inputs and outputs of power driver circuit 200 and various operational aspects of power driver circuit 200. For example, controller 214 may monitor AC voltage/frequency of electrical power received at input terminal 201 (e.g., the electrical power received from distribution network 108), the voltage/frequency of AC line 226, the voltage of DC bus 212, the voltage of DC storage capacitor 234, the energy storage of mechanical energy device 242, the energy storage of chemical energy device 252, and the dissipation capacity of dissipation device 262. Further, controller 214 may control operations of converters 222, 232, 240, 250 and 260 to employ the desired energy receipt, storage, absorption/dissipation, and generation such that power driver can be used to effectively sink excess power (e.g., absorb/dissipate power) from distribution network 108 and/or supply supplemental/backup power to distribution network 108.

Although the illustrated embodiment includes one of each of a mechanical energy circuit, a chemical energy circuit and a power dissipation circuit, embodiments may include any suitable number or combination of the described circuits. For example, an embodiment may include a mechanical energy circuit, a chemical energy circuit or a power dissipation circuit but not include the other two types of circuits. That is, for example, an embodiment may include one or more mechanical energy circuits, but not include either of a chemical energy circuit and a power dissipation circuit. In yet another example, an embodiment may include a combination of some but not all of a mechanical energy circuit, a chemical energy circuit and a power dissipation circuit. That is, for example, an embodiment may include one or more mechanical energy circuits and one or more chemical energy circuits, but not include a power dissipation circuit. The configuration of a power driver circuit may be based on requirements of the particular application, including, for example, energy storage, supply, and/or dissipation capacity requirements.

Figure 3:
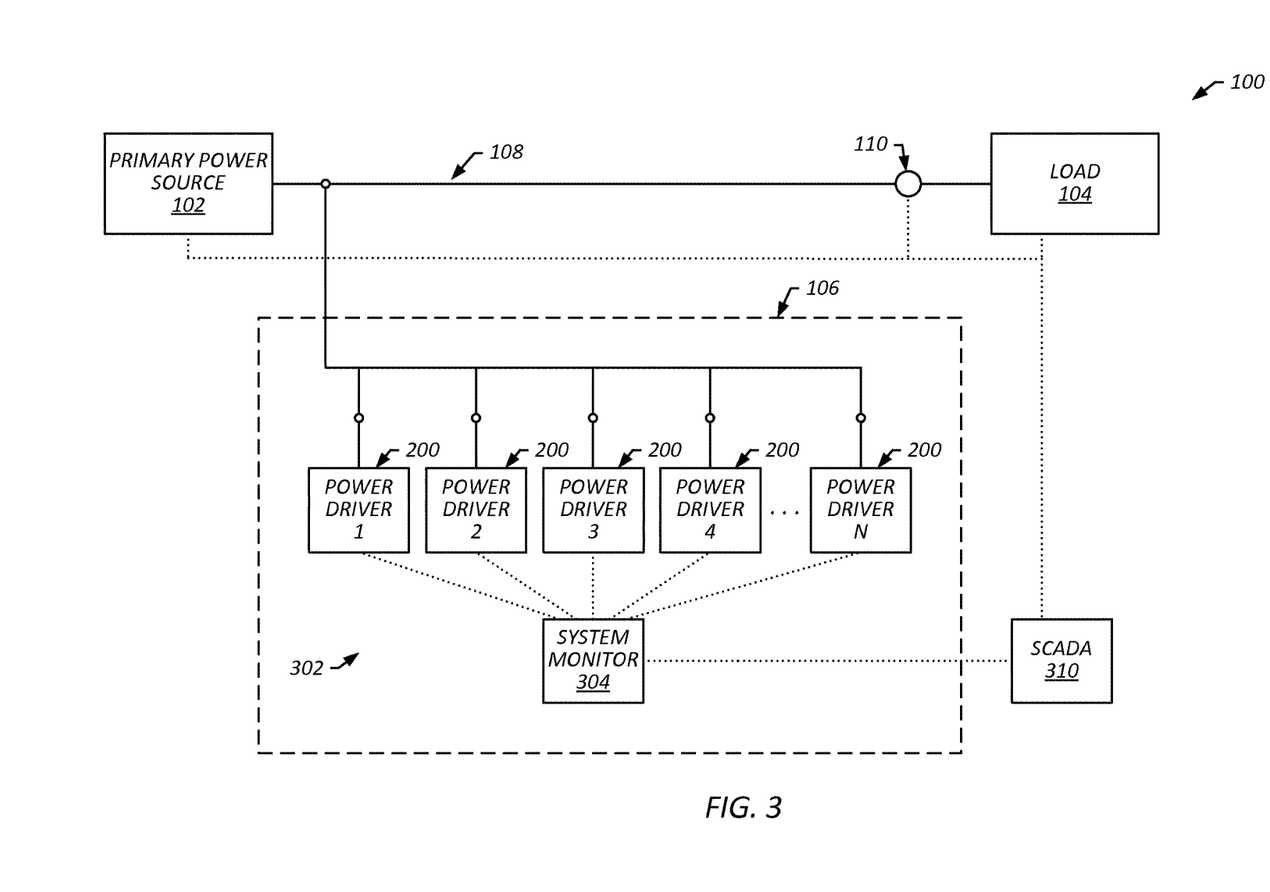
FIG. 3 is a diagram that illustrates a UPS employing parallel power driver circuits (a "parallel on-line system") in accordance with one or more embodiments of the present technique.

In some embodiments, multiple power driver circuits can be employed to provide increased capacity and/or to provide redundancy, thereby improving the robustness of the system. FIG. 3 is a diagram that illustrates UPS 100 employing parallel power driver circuits (referred to herein as a "parallel on-line system") in accordance with one or more embodiments of the present technique. In the illustrated embodiment, parallel on-line system 100 includes secondary power source 106 including a parallel power driver system 302 and a system monitor 304. As depicted, in some embodiments, parallel power driver system 302 includes two or more power driver circuits 200 (e.g., 1, 2, 3, 4 . . . N power driver circuits 200) coupled in parallel to the power distribution network 108. Each of power drivers 200 may be the same or similar to the embodiments of power driver circuit 200 described above with regard to FIG. 2. During operation, some or all of power driver circuits 200 may be operated in parallel to provide increased capacity for supplying power to and/or sinking power from distribution network 108.

If, for example, each of power driver circuit 200 of parallel power driver system 302 of has the capacity to supply approximately 750 watts for a given period of time (e.g., approximately 10 seconds), four power driver circuits 200 can be coupled to a distribution network to supply approximately 3000 watts for the given period of time (e.g., 10 seconds), or to provide approximately 750 watts over an extended period of time (e.g., approximately 40 seconds). Similarly, if, for example, each of power driver circuit 200 of parallel power driver system 302 has the capacity to sink approximately 200 watts for a given period of time (e.g., approximately 10 seconds), four power driver circuits 200 can be coupled to a distribution network to sink approximately 800 watts for the given period of time (e.g., 10 seconds), or to sink 200 watts over an extended period of time (e.g., approximately 40 seconds). Moreover, the use of multiple power driver circuits 200 can be employed to provide redundancy for secondary power source 106, thereby improving the robustness of UPS 100. For example, if parallel power driver system 302 includes four power driver circuits 200 coupled to distribution network 108 and one of the power driver circuits 200 is taken offline (e.g., for repair or due to failure), the other three power driver circuits 200 can continue to supply supplemental power to the distribution network and/or sink excess power from distribution network 108 as needed.

In some embodiments, system monitor 304 is employed to monitor and/or control operations of power drivers 200 of parallel power driver system 302. For example, system monitor 314 may communicate with the respective controllers 212 to monitor the power supply capacities, power sinking capacities and other characteristics of each of power driver circuits 200 monitored by controllers 212, and/or may communicate with the respective controllers 212 to control operations of power drivers 200. In some embodiments, system monitor 304 coordinates operations of the various power driver circuits 200. If, for example, a small disturbance is detected (e.g., a small voltage spike or drop on distribution network 108 is detected) that is within the capacity of single power driver circuit 200, system monitor 304 may command one of power driver circuits 200 to respond by supplying supplemental power or sinking the excess power. If, for example, a large disturbance is detected (e.g., a large voltage spike or drop on distribution network 108 is detected) that is not within the capacity of single power driver circuit 200, system monitor 304 may command some or all of the of power driver circuits 200 to respond by supplying supplemental power or sinking the excess power.

UPS 100 may include a Supervisory Control and Data Acquisition system ("SCADA") 310. In some embodiments, SCADA 310 includes a high-level monitor for monitoring and/or controlling operations of entities of UPS 100. For example, SCADA may monitor/control operations and output of primary supply 102, voltage/frequency of electrical power on distribution network 108, operations of meter 110, operations and power requirements of load 104, and/or operations and power supply/sinking capacity of secondary source 106. In some embodiments, monitoring and control of secondary source 106 is facilitated by controller 214 of power driver circuits 200 and/or system monitor 304.

Figure 4:
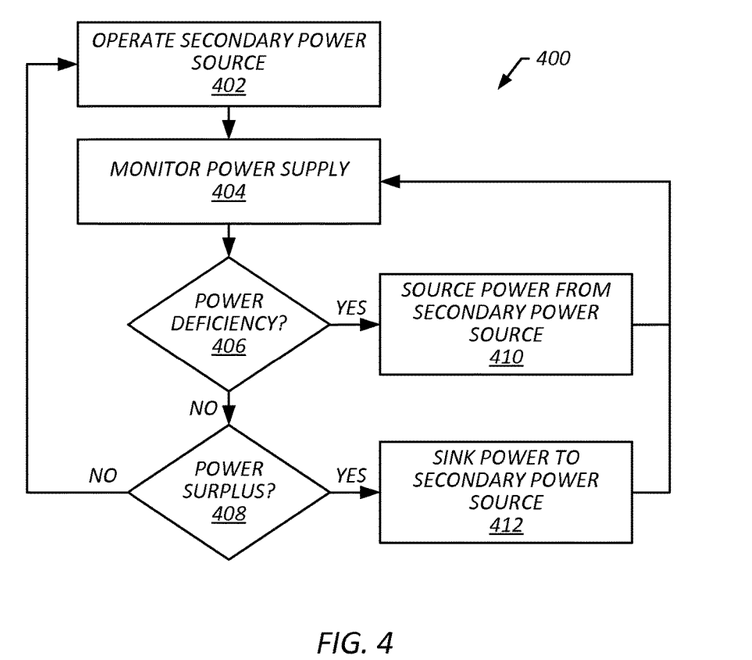
FIG. 4 is a flowchart that illustrate a method for supplying power in accordance with one or more embodiments of the present technique.

FIG. 4 is a flowchart that illustrates a method for supplying power in accordance with one or more embodiments of the present technique. Method 400 may be employed by a secondary source 106. For example, method 400 may be employed by controller 214 of power driver circuit 200. Method 400 generally includes operating a secondary power source (block 402), monitoring a power supply (block 404) to determine whether a power deficiency/shortage or a power surplus exists (block 406 and 408), and in response to determining that a power deficiency exists, sourcing power from the secondary power source (block 410), and/or in response to determining that a power surplus exists, sinking power to the secondary power source (block 412).

In some embodiments, operating a secondary power source (block 402) includes maintaining backup power sources in a state that enables them to source power to and/or sink power as required. For example, with regard to mechanical energy circuit 204, operating a secondary power source may include operating mechanical energy device 242 in a state that enables it to source/supply supplemental power to and/or sink excess power from distribution network 108.

In an embodiment in which mechanical energy circuit 204 is used to source supplemental power, operating a secondary power source may include operating mechanical energy device 242 at an normal operational state to store a relatively large amount of mechanical energy (e.g., up to a maximum rated energy storage for the device) that can be used to generate a relatively large amount of power (e.g., up to a maximum rated power output for the device) that can be supplied to distribution network 108. For example, in an embodiment in which mechanical energy device 242 includes a flywheel system having a flywheel with a maximum rated operational speed of 7700 rpm that corresponds to a maximum rated output of 750 W, the flywheel may be maintained at 7700 rpm, such that it can generate an supply a maximum rated amount of power (e.g., approximately 750 W). After the flywheel is used to source power, the flywheel can be returned to its operating speed. For example, if sourcing power reduced the speed of the flywheel to 5000 rpm and there is no longer a need to source power (e.g., the voltage drop on distribution network 108 has passed), operation of the circuit may include driving the flywheel (e.g., using power from distribution network 108) to bring the flywheel back to its operational speed (e.g., 7700 rpm) such that it is again ready to source power.

In an embodiment in which mechanical energy circuit 204 is used to sink excess power, operating a secondary power source may include operating mechanical energy device 242 at a reduced operational state. Operating the at a reduced operational state may enable mechanical energy device 242 to both store mechanical energy (e.g., that can be used to generate power for supply to distribution network 108), and absorb/dissipate excess power (e.g., absorb/dissipate power received from distribution network 108) while operating within operational limits. For example, in an embodiment in which mechanical energy device 242 includes a flywheel system having a flywheel with a maximum rated operational speed of 7700 rpm that corresponds to a maximum rated output of 750 W, the flywheel may be maintained at reduced operating speed of 6000 rpm, such that it can generate an supply a relatively moderate/reduced amount of power (e.g., approximately 600 W), while still maintaining the ability to absorb/dissipate energy via driving the flywheel using the excess power. Thus, for example, if the using excess energy from distribution network 108 results in the flywheel increasing in speed from 6000 rpm to 7000 rpm, the flywheel is still operating within the rated limits for the flywheel. In such an embodiment, the speed of the flywheel can be subsequently reduced (e.g., reduced to the reduced operational speed of 6000 rpm), thereby allowing the flywheel to continue to both absorb/dissipate excess energy and generate power. After the flywheel is used to sink power, the flywheel can be returned to its operating speed. For example, if sinking power increased the speed of the flywheel to 7000 rpm and there is no longer a need to source power (e.g., the voltage spike on distribution network 108 has passed), operation of the circuit may include allowing the flywheel to return to its operational speed (e.g., 6000 rpm) such that it is again ready to sink power. This may be accomplished by, for example, removing or decreasing power to the motor.

With regard to chemical energy circuit 206, operating a secondary power source may include maintaining chemical energy device 252 in a state that enables it to source supplemental power to distribution network 108. For example, in an embodiment in which chemical energy device 252 includes a battery (or ultracpacitor), operating a secondary power source may include mainlining the battery (or ultracpacitor) in a charged state. The energy stored in the battery (or ultracpacitor) can be used to generate supplemental power that can be supplied to distribution network 108.

With regard to storage capacitor 234, operating a secondary power source may include maintaining storage capacitor 234 in a charged state that enables it to source supplemental power to distribution network 108. For example, operating a secondary power source may include energizing DC bus 212 to charge storage capacitor 234 and maintain storage capacitor 234 in a charged state. The energy stored in storage capacitor 234 can be used to generate supplemental power that can be supplied to distribution network 108.

In some embodiments, monitoring a power supply to determine whether a power deficiency or a power surplus exists (block 404) includes monitoring power on distribution network 108 to determine whether a power deficiency/ shortage or a power surplus exists. For example, with regard to UPS 100, monitoring a power supply to determine whether a power deficiency or a power surplus exists may include monitoring the voltage level and/or frequency of the power at input terminal 201. In some embodiments, a power deficiency is determined to exists if the voltage is below a threshold voltage value and/or a frequency is below a threshold frequency value. Conversely, in some embodiments, a power surplus is determined to exists if the voltage is above a threshold voltage value and/or a frequency is below a threshold frequency value.

In response to determining that neither a power deficiency nor a power surplus exists, method 400 may include returning to operating a secondary power source (block 402). For example, in response to determining that neither a power deficiency nor a power surplus exists, the secondary power source(s) can be maintained in their normal operating states, including energizing DC bus 212 to maintain the charge of storage capacitor 234, driving the motor of the flywheel system (using power from distribution network 108) to maintain the flywheel at its operational speed (e.g., 7700 rpm or 6000 rpm), and maintaining the charge of the battery (or ultracpacitor) using power from distribution network 108.

In response to determining that a power deficiency exists, method 400 may include proceeding to sourcing power from the secondary power source (block 410). In some embodiments, sourcing power from the secondary power source includes secondary source 106 supplying power to distribution network 108. For example, sourcing power from secondary power source may include supplying distribution network 108 with power generated by storage capacitor 234, mechanical energy circuit 206 and/or chemical energy circuit 208. With regard to storage capacitor 234, in some embodiments, sourcing power from the secondary power source includes discharging capacitor 234 to generate electrical power that is routed to power distribution network 108. With regard to mechanical energy circuit 206, in some embodiments, sourcing power from the secondary power source includes operating mechanical energy device 452 to convert mechanical energy stored to electrical power that is routed to power distribution network 108. For example, mechanical energy stored via rotation of the flywheel can be converted (e.g., by a generator the flywheel system) to electrical energy that is supplied to distribution network 108 via converter 240, DC bus 212, power conditioner circuit 204, and I/O circuit 202. With regard to chemical energy circuit 206, in some embodiments, sourcing power from the secondary power source includes operating chemical energy device 252 to convert chemical energy stored to electrical power that is routed to power distribution network 108. For example, chemical energy stored by battery (or ultracpacitor) can be converted to electrical energy that is supplied to distribution network 108 via converter 250, DC bus 212, power conditioner circuit 204, and I/O circuit 202.

As depicted, monitoring of the power supply may continue to occur, and sourcing of power from the secondary source may continue to occur as long as a power deficiency exists. In some instances, it may be determined that the deficiency dos not exists when the power on distribution network returns to normal levels (e.g., within acceptable ranges of voltage and frequency). For example, sourcing of power from the secondary source may continue to occur until the primary source is operating normally, or another primary source (e.g., a back-up generator) is brought on-line to supply power to maintain distribution network 108 at normal voltage levels and frequency. In many instances, the duration of a power deficiency is several seconds or less (e.g., during a brief power outage), with many lasting for only a fraction of a second (e.g., during a voltage spike/drop).

In some embodiments, a control algorithm is used to regulate/prioritize how power is sourced. For example, a priority based control algorithm may include a hierarchical scheme, including storage capacitor 234 having a first-level priority, mechanical energy circuit 206 having a second-level priority, and chemical energy circuit 206 having a third-level priority. In such an embodiment, sourcing power from the secondary power source may include, first, supplying power generated using energy stored by storage capacitor 234, second, (e.g., once energy stored by storage capacitor 234 is depleted below a threshold level) operating mechanical energy circuit 206 to supply power using energy stored by mechanical energy device 452 and, third (e.g., once energy stored by mechanical energy circuit 206 is depleted below a threshold level) operating chemical energy circuit 206 to supply power using energy stored by chemical energy device 252. Such a hierarchical-priority scheme may be especially beneficial in cases where certain energy sources are more/less suitable to repeated use. For example, some devices may experience a degradation in performance the more times they are "hit" (e.g., used to source energy). For example, a storage capacitor may experience little to no performance degradation as a result of repeated hits, a mechanical energy device (e.g., a flywheel system) may experience low degradation as a result of repeated hits, and a chemical energy device (e.g., a battery) may experience mild to high degradation as a result of repeated hits. As a result devices such as batteries may need to be replaced more often the more often they are discharged to supply power. This can lead to an exponential increase in cost, especially if batteries are expensive and difficult to replace. Using a hierarchical-priority scheme such as that described herein may ensure that the majority of hits occur to devices that are less susceptible to performance degradation.

In response to determining that a power surplus exists, method 400 may include proceeding to sinking power to the secondary power source (block 412). In some embodiments, sinking power from the secondary power source includes secondary source 106 absorbing/dissipating power received from distribution network 108. For example, sinking power from secondary power source may include dissipating power via mechanical energy circuit 206 and/or dissipation circuit 210.

With regard to mechanical energy circuit 206, in some embodiments, sinking power to the secondary power source includes operating mechanical energy device 242 to convert electrical power received from distribution network 108 to mechanical energy. For example, a flywheel system can use excess electrical energy received from distribution network 108 to drive the motor, thereby spinning the flywheel and converting the electrical energy to mechanical energy stored via rotation of the flywheel.

With regard to power dissipation circuit 210, in some embodiments, sinking power to the secondary power source includes operating power dissipation circuit 210 to convert electrical power received from distribution network 108 to heat or another form of energy that can be dissipated. For example, excess electrical energy received from distribution network 108 can be routed through dissipation device (e.g., a resistor) to generate heat that dissipates as thermal energy.

In some embodiments, a control algorithm is used to regulate/prioritize how power is sinked. For example, a priority based control algorithm may include a hierarchical scheme, including mechanical energy circuit 206 having a first-level priority, and power dissipation circuit 210 having a second-level priority. In such an embodiment, sinking power to the secondary power source may include, first, operating mechanical energy circuit 206 to sink power received from distribution network 108, and second, (e.g., if the sinking capacity of the mechanical energy circuit 206 is exceeded) operating power dissipation circuit 210 to sink power received from distribution network 108. Such a priority scheme may be especially beneficial in cases where use of certain energy sinks is more desirable. For example, if an implementation is sensitive to heat build-up (e.g., in an enclosure), it may be less desirable to dissipate energy via power dissipation circuit 210.

It will be appreciated that method 400 is an exemplary embodiment that may be employed in accordance with techniques described herein. Methods 400 may be modified to facilitate variations of its implementations and uses. The order of the steps and operations described with regard to method 400 may be modified, and various elements may be added, reordered, combined, omitted, modified, etc. In some embodiments, method 400 is employed by controller 214, monitor 304, and/or SCADA 310. Method 400 may be implemented in software, hardware, or a combination thereof. Some or all of the methods 600 and 700 may be implemented by one or more of the modules/applications described herein. Controller 214, monitor 304, and/or SCADA 310 may be employed using one or more computer devices, such as computer device 500 described herein at least with regard to FIG. 5.

Figure 5:
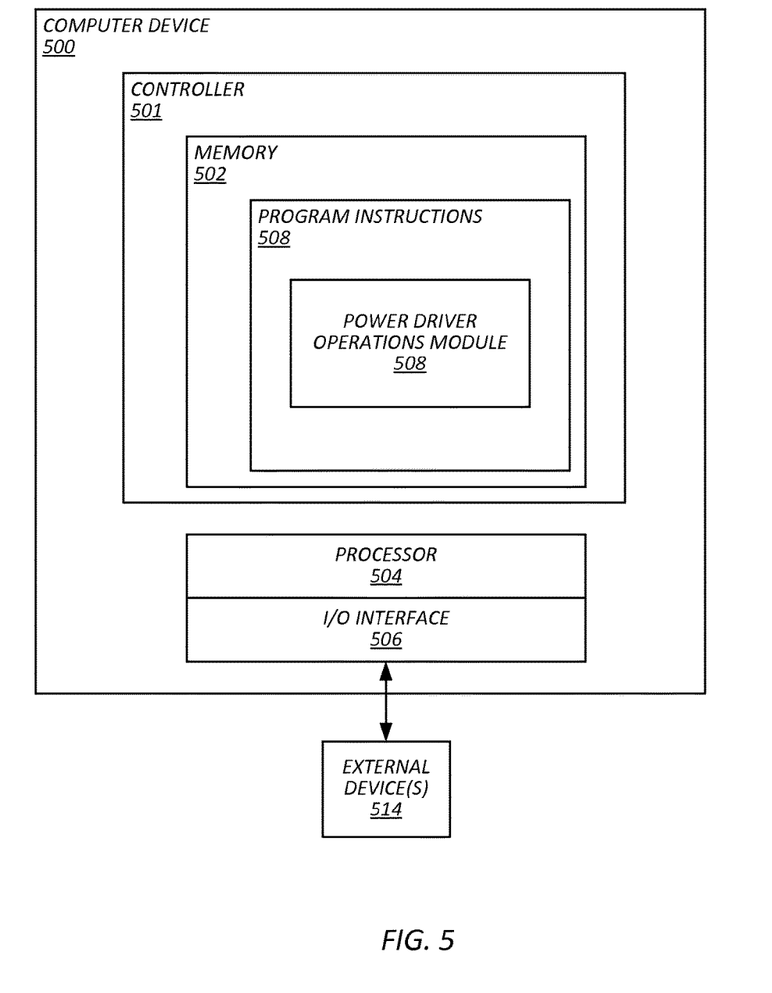
FIG. 5 is a block diagram that illustrates a computer device in accordance with one or more embodiments of the present technique.

FIG. 5 is a block diagram that illustrates computer device 500 in accordance with one or more embodiments of the present technique. In some embodiments, computer device 500 includes a controller 501 for controlling the operational aspects of power driver circuit 200. In some embodiments, controller 501 includes a memory 502, a processor 504 and an input/output (I/O) interface 506. Memory 502 may include non-volatile memory (e.g., flash memory, ROM, PROM, EPROM, EEPROM memory), volatile memory (e.g., random access memory (RAM), static random access memory (SRAM), synchronous dynamic RAM (SDRAM)), bulk storage memory (e.g., CD-ROM and/or DVD-ROM, hard-drives), or the like. Memory 502 may include a non-transitory computer readable storage medium having program instructions 508 stored thereon that are executable by a computer processor (e.g., processor 504) to cause the functional operations (e.g., methods/routines/processes) described herein, including those described with regard to controller 214, monitor 304, and/or SCADA 310. Program instructions 508 may include modules including program instructions that are executable by processor 504 to provide some or all of the functionality described herein with regard to UPS 100, controller 214, monitor 304, and/or SCADA 310. Program instructions 508 may include, for example, a power driver operations module 510 for performing some or all of the operational aspects of method 400 (described herein with regard to at least FIG. 4).

Processor 504 may be any suitable processor capable of executing/performing program instructions. Processor 504 may include a central processing unit (CPU) that carries out program instructions (e.g., program instructions of module 510) to perform arithmetical, logical, and input/output operations of computer device 500, including those described herein. I/O interface 506 may provide an interface for communication with of one or more external devices 514 (e.g., primary source 102, load 104, SCATA 310, monitor 304, controller 214, power conditioner circuit 204, mechanical energy circuit 206, chemical energy circuit 208, power dissipation circuit 210), and/or the like. external devices may include a mouse/keyboard/touchscreen, a graphical user interface (GUI), and/or the like. Devices may be connected to I/O interface 506 via a wired or wireless connection.

Various embodiments may further include receiving, sending or storing instructions and/or data implemented in accordance with the foregoing description upon a computer-accessible medium. Generally speaking, a computer-accessible/readable storage medium may include a non-transitory storage media such as magnetic or optical media, (e.g., disk or DVD/CD-ROM), volatile or non-volatile media such as RAM (e.g. SDRAM, DDR, RDRAM, SRAM, etc.), ROM, etc., as well as transmission media or signals such as electrical, electromagnetic, or digital signals, conveyed via a communication medium such as network and/or a wireless link.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed or omitted, and certain features of the invention may be utilized independently, all as would be apparent to one skilled in the art after having the benefit of this description of the invention. Changes may be made in the elements described herein without departing from the spirit and scope of the invention as described in the following claims. Headings used herein are for organizational purposes only and are not meant to be used to limit the scope of the description.

As used throughout this application, the word "may" is used in a permissive sense (i.e., meaning having the potential to), rather than the mandatory sense (i.e., meaning must). The words "include", "including", and "includes" mean including, but not limited to. As used throughout this application, the singular forms "a", "an" and "the" include plural referents unless the content clearly indicates otherwise. Thus, for example, reference to "an element" includes a combination of two or more elements. Unless specifically stated otherwise, as apparent from the discussion, it is appreciated that throughout this specification discussions utilizing terms such as "processing", "computing", "calculating", "determining" or the like refer to actions or processes of a specific apparatus, such as a special purpose computer or a similar special purpose electronic processing/computing device. In the context of this specification, a special purpose computer or a similar special purpose electronic processing/computing device is capable of manipulating or transforming signals, typically represented as physical electronic or magnetic quantities within memories, registers, or other information storage devices, transmission devices, or display devices of the special purpose computer or similar special purpose electronic processing/computing device.

In this patent, certain U.S. patents, U.S. patent applications, or other materials (e.g., articles) have been incorporated by reference. The text of such U.S. patents, U.S. patent applications, and other materials is, however, only incorporated by reference to the extent that no conflict exists between such material and the statements and drawings set forth herein. In the event of such conflict, any such conflicting text in such incorporated by reference U.S. patents, U.S. patent applications, and other materials is specifically not incorporated by reference in this patent.

What is claimed is:

1. A uninterruptable electrical power supply system comprising:
   an electrical power distribution network comprising:
      a consumer side network configured to couple to one or more electrical loads and configured to consume electrical power;
      a utility side network configured to supply electrical power to the consumer side network; and
      a terminal coupled between the consumer side network and the utility side network;
   a primary power source coupled to the utility side network, wherein the primary power source is configured to supply electrical power to the utility side network for supply to the consumer side network; and
   a secondary power source coupled to the utility side network and including a power dissipation circuit and at least two power driver circuits, wherein the secondary power source is configured to:
      supply, in response to a power shortage on the utility side network, backup power to the utility side network from each of the power driver circuits based on a hierarchical-priority for sourcing power, wherein energy stored in a first power driver circuit selected with a first priority for sourcing power is substantially sourced to supply backup power prior to sourcing energy stored in a second power driver circuit selected with a second priority for sourcing power, the second priority for sourcing power being lower than the first priority for sourcing power; and
      sink, in response to a power surplus on the utility side network, surplus power from the utility side network to at least two circuits selected from the power driver circuits and the power dissipation circuit based on a hierarchical-priority for sinking power, wherein energy is stored in the first power driver circuit selected with a first priority for sinking power to sink surplus power prior to either storing energy in the second power driver circuit selected with a second priority for sinking power or dissipating power with the power dissipation circuit selected with a third priority for sinking power, the second priority and the third priority for sinking power being lower than the first priority,
   wherein each of the at least two power driver circuits is selected at a given priority in the hierarchical-priority for sourcing power and the hierarchical-priority for sinking power based at least in part on a resiliency to repeated sourcing and sinking cycles, the first power driver circuit being more resilient to repeated sourcing and sinking cycles than the second power driver circuit, and
   wherein the power dissipation circuit is selected at a given priority in the hierarchical-priority for sinking power based at least in part on a response of one or more of the at least two power driver circuits to the power surplus on the utility side network.

2. The system of claim 1, wherein the at least two power driver circuits are selected from:
   a power conditioner circuit comprising a storage capacitor configured to store energy in an electrical form and having a first resiliency to repeated sourcing and sinking cycles;
   mechanical energy circuit comprising a mechanical energy storage device configured to store energy in a mechanical form and having a second resiliency to repeated sourcing and sinking cycles; and
   chemical energy circuit comprising a chemical energy storage device configured to store energy in a chemical form and having a third resiliency to repeated sourcing and sinking cycles; and
   wherein the power dissipation circuit is configured to dissipate energy not stored in at least one of the power driver circuits.

3. The system of claim 2, wherein the at least two power driver circuits and the power dissipation circuit are coupled in parallel to the electrical power distribution network.

4. The system of claim 2, wherein the mechanical energy circuit comprises:
   a flywheel configured to rotate to store mechanical energy;
   a motor configured to drive rotation of the flywheel using the electrical power supplied by the primary power source; and
   a generator configured to convert the mechanical energy of the flywheel into electrical energy supplied to the utility side network as the backup power.

5. The system of claim 4, wherein supplying the backup power to the utility side network comprises the generator converting the mechanical energy of the flywheel into the electrical energy supplied to the utility side network as the backup power.

6. The system of claim 4, wherein sinking the surplus power from the utility side network comprises the motor driving rotation of the flywheel using the electrical power supplied by the primary power source.

7. The system of claim 2, wherein the chemical energy circuit comprises one or more batteries.

8. The system of claim 2, wherein the chemical energy circuit comprises one or more ultracapacitors.

9. The system of claim 2, wherein the power dissipation circuit comprises a resistance device configured to dissipate energy in the form of heat.

10. The system of claim 2, wherein the secondary power source comprises at least three power driver circuits and is configured to:
    supply, in response to a first level power shortage, the backup power derived from the energy stored by the storage capacitor, wherein the storage capacitor is the first power driver circuit selected with the first priority for sourcing power;

supply, in response to a second level power shortage that is greater than the first level power shortage, the backup power derived from the energy stored by the mechanical energy storage device, wherein the mechanical energy storage device is the second power driver circuit selected with the second priority for sourcing power; and supply, in response to a third level power shortage that is greater than the first and second level power shortages, the backup power derived from the energy stored by the chemical energy storage device, wherein the chemical energy storage device is a third power driver circuit selected with a third priority for sourcing power, the third priority for sourcing power being lower than the first priority and the second priority for sourcing power.

11. The system of claim 1, wherein the secondary power source is housed in a self-contained unit that is separate from the primary power source.

12. A uninterruptable electrical power supply system comprising:

a secondary power source configured to be coupled to a power distribution network comprising a primary power source configured to supply electrical power to the power distribution network, the secondary power source including at least two power driver circuits, wherein the secondary power source is configured to:

supply, in response to a power shortage on the power distribution network, backup power to the power distribution network from each of the power driver circuits based on a hierarchical-priority for sourcing power, wherein energy stored in a first power driver circuit selected with a first priority for sourcing power is substantially sourced to supply backup power prior to sourcing energy stored in a second power driver circuit selected with a second priority for sourcing power, the second priority for sourcing power being lower than the first priority for sourcing power; and sink, in response to a power surplus on the power distribution network, surplus power from the power distribution network to the at least two power driver circuits based on a hierarchical-priority for sinking power, wherein energy is stored in the first power driver circuit selected with a first priority for sinking power to sink surplus power prior to storing energy in the second power driver circuit selected with a second priority for sinking power, the second priority for sinking power being lower than the first priority, and wherein each of the at least two power driver circuits is selected at a given priority in the hierarchical-priority for sourcing power and the hierarchical-priority for sinking power based at least in part on a resiliency to repeated sourcing and sinking cycles, the first power driver circuit being more resilient to repeated sourcing and sinking cycles than the second power driver circuit.

13. The system of claim 12, wherein the at least two power driver circuits are selected from:

a power conditioner circuit comprising a storage capacitor configured to store energy in an electrical form and having a first resiliency to repeated sourcing and sinking cycles;

mechanical energy circuit comprising a mechanical energy storage device configured to store energy in a mechanical form and having a second resiliency to repeated sourcing and sinking cycles; and chemical energy circuit comprising a chemical energy storage device configured to store energy in a chemical form and having a third resiliency to repeated sourcing and sinking cycles; and wherein a power dissipation circuit is configured to dissipate energy not stored in at least one of the power driver circuits, the power dissipation circuit selected at a given priority in the hierarchical-priority for sinking power based at least in part on a response of one or more of the at least two power driver circuits to the power surplus on the power distribution network.

14. The system of claim 13, wherein the at least two power driver circuits and the power dissipation circuit are coupled in parallel to the power distribution network.

15. The system of claim 13, wherein the mechanical energy circuit comprises:

a flywheel configured to rotate to store mechanical energy;

a motor configured to drive rotation of the flywheel using the electrical power supplied by the primary power source; and a generator configured to convert the mechanical energy of the flywheel into electrical energy supplied to the power distribution network as the backup power.

16. The system of claim 15, wherein supplying the backup power to the power distribution network comprises the generator converting the mechanical energy of the flywheel into the electrical energy supplied to the power distribution network as the backup power.

17. The system of claim 15, wherein sinking the surplus power from the power distribution network comprises the motor driving rotation of the flywheel using the electrical power supplied by the primary power source.

18. The system of claim 13, wherein the chemical energy circuit comprises one or more batteries.

19. The system of claim 13, wherein the chemical energy circuit comprises one or more ultracapacitors.

20. The system of claim 13, wherein the power dissipation circuit comprises a resistance device configured to dissipate energy in the form of heat.

21. The system of claim 13, wherein the secondary power source comprises at least three power driver circuits and is configured to:

supply, in response to a first level power shortage, the backup power derived from the energy stored by the storage capacitor, wherein the storage capacitor is the first power driver circuit selected with the first priority for sourcing power;

supply, in response to a second level power shortage that is greater than the first level power shortage, the backup power derived from the energy stored by the mechanical energy storage device, wherein the mechanical energy storage device is the second power driver circuit selected with the second priority for sourcing power; and supply, in response to a third level power shortage that is greater than the first and second level power shortages, the backup power derived from the energy stored by the chemical energy storage device, wherein the chemical energy storage device is a third power driver circuit selected with a third priority for sourcing power, the third priority for sourcing power being lower than the first priority and the second priority for sourcing power.

22. The system of claim 12, wherein the secondary power source is housed in a self-contained unit that is separate from the primary power source.

23. A method for providing uninterrupted power via a power distribution network comprising a secondary power source configured to supply backup power to the power distribution network, the secondary power source including at least two power driver circuits, the method comprising operating the secondary power source to:
supply, in response to a power shortage on the power distribution network, backup power to the power distribution network from each of the power driver circuits based on a hierarchical-priority for sourcing power, wherein energy stored in a first power driver circuit selected with a first priority for sourcing power is substantially sourced to supply backup power prior to sourcing energy stored in a second power driver circuit selected with a second priority for sourcing power, the second priority for sourcing power being lower than the first priority for sourcing power; and
sink, in response to a power surplus on the power distribution network, surplus power from the power distribution network to the at least two power driver circuits based on a hierarchical-priority for sinking power, wherein energy is stored in the first power driver circuit selected with a first priority for sinking power to sink surplus power prior to storing energy in the second power driver circuit selected with a second priority for sinking power, the second priority for sinking power being lower than the first priority, and
wherein each of the at least two power driver circuits is selected at a given priority in the hierarchical-priority for sourcing power and the hierarchical-priority for sinking power based at least in part on a resiliency to repeated sourcing and sinking cycles, the first power driver circuit being more resilient to repeated sourcing and sinking cycles than the second power driver circuit.

24. The method of claim 23, wherein the at least two power driver circuits are selected from:
a power conditioner circuit comprising a storage capacitor configured to store energy in an electrical form and having a first resiliency to repeated sourcing and sinking cycles;
mechanical energy circuit comprising a mechanical energy storage device configured to store energy in a mechanical form and having a second resiliency to repeated sourcing and sinking cycles; and
chemical energy circuit comprising a chemical energy storage device configured to store energy in a chemical form and having a third resiliency to repeated sourcing and sinking cycles; and
wherein a power dissipation circuit is configured to dissipate energy not stored in at least one of the power driver circuits, the power dissipation circuit selected at a given priority in the hierarchical-priority for sinking power based at least in part on a response of one or more of the at least two power driver circuits to the power surplus on the power distribution network.

25. The system of claim 1, wherein selecting each of the at least two power driver circuits at a given priority in the hierarchical-priority for sourcing power and the hierarchical-priority for sinking power further comprises:
selecting a next power driver circuit at a next lower priority based in part on reaching a minimum or a maximum energy storage capacity in a currently selected power driver circuit; or
selecting a next power driver circuit at a next lower priority or the power dissipation circuit based in part on reaching a maximum sinking or sourcing capacity in a currently selected power driver circuit.

26. The system of claim 1, wherein the first power driver circuit is a mechanical energy circuit comprising a mechanical energy storage device configured to store energy in a mechanical form and the second power driver circuit is a chemical energy circuit comprising a chemical energy storage device configured to store energy in a chemical form.

27. The system of claim 26, wherein the power dissipation circuit is selected to dissipate energy in response to a maximum sinking capacity of at least the mechanical energy storage device in response to a voltage spike in the power surplus received from the utility side network.

28. The system of claim 27, wherein the power dissipation circuit comprises a resistance device configured to dissipate energy in the form of heat.

* * * * *